United States Patent [19]

Schulz et al.

[11] 4,456,348
[45] Jun. 26, 1984

[54] APPARATUS FOR EXAMINING EYES

[75] Inventors: Kurt Schulz; Peter Maglica, both of Oberkochen, Fed. Rep. of Germany

[73] Assignee: Carl Zeiss-Stiftung, Oberkochen, Fed. Rep. of Germany

[21] Appl. No.: 197,982

[22] PCT Filed: Jan. 12, 1980

[86] PCT No. PCT/DE80/0003

§ 371 Date: Oct. 16, 1980

§ 102(e) Date: Oct. 6, 1980

[87] PCT Pub. No. WO80/01642

PCT Pub. Date: Aug. 21, 1980

[30] Foreign Application Priority Data

Feb. 16, 1979 [DE] Fed. Rep. of Germany ....... 2905915

[51] Int. Cl.³ .............................................. A61B 3/10
[52] U.S. Cl. .................................. 351/212; 350/520; 350/587; 351/205; 351/214
[58] Field of Search ................... 351/6, 14, 18, 37, 38, 351/39, 205, 206, 211, 212, 214, 221; 350/514, 520, 521, 522, 559, 587

[56] References Cited

U.S. PATENT DOCUMENTS

| 1,283,963 | 11/1918 | Takahashi | 350/587 |
| 1,547,142 | 7/1925 | Bausch | 350/587 |
| 2,235,319 | 3/1941 | Jobe | 351/38 |
| 3,652,153 | 3/1972 | Gambs | 351/14 |
| 3,831,285 | 8/1974 | Vissing | 350/587 |
| 4,315,672 | 2/1982 | Muller et al. | 351/14 |

Primary Examiner—R. A. Rosenberger

[57] ABSTRACT

In an instrument for examination of the eye, which consists of a binocular telescopic magnifier and of an ophthalmological examination instrument, the main objective of the binocular telescopic magnifier is arranged in a swingable mount and can be swung out of the optical ray path. The mount is provided with a connecting piece to receive an ophthalmological instrument which can be swung into the ray path in the place of the main objective. In this way a rapid change is made possible from one diagnostic instrument to another, for instance from a slit lamp to an ophthalmometer.

4 Claims, 3 Drawing Figures

APPARATUS FOR EXAMINING EYES

The present invention relates to a combination instrument for the examination of the eye, consisting of a binocular telescopic magnifier and of an ophthalmological or ophthalmometric examination instrument. In ophthalmological instruments the development is tending towards combination instruments by which efficient operation in minimum space is possible.

From West German Pat. No. 26 14 273 it is known to combine an ophthalmometer with a binocular telescopic magnifier in such a manner that the optical system of the ophthalmometer can be adjusted rather than the main objective of the binocular telescopic magnifier. Such a combination instrument has the disadvantage that when switching from slit lamp to ophthalmometer and vice versa the main objective must be detached from a connecting part and replaced by the ophthalmometer attachment. The placing on and off of the parts of the instrument will be tolerated only by a group of users who do not have to effect the change too frequently.

The object of the present invention is therefore to provide a combination instrument which permits rapid change from one diagnostic instrument to the other, for instance from a slit lamp to an ophthalmometer.

This object is achieved in accordance with the invention in the manner that the main objective of the binocular telescopic magnifier is arranged in a mount which is supported for swinging around a horizontal axis out of the position in which it is present in the optical ray path and that the mount is provided with a connecting piece to receive an ophthalmological instrument.

If the main objective is located in operating position in the optical ray path then the binocular telescopic magnifier acts together with a slit lamp and forms a slit-lamp instrument.

In one suitable embodiment of the invention, the slit lamp is swingable around a vertical axis and can be swung into and out of the ray path of the binocular telescopic magnifier. The connecting piece which is attached to the mount of the main objective is advisedly developed as a receiving dovetail. An insertion piece which fits this dovetail receiver can be fastened to a part of the ophthalmometer which can be connected to the combination instrument.

If such an opthalmometer part is so connected with the objective mount of the binocular telescopic magnifier that when the objective is swung up into its position of rest said part is itself swung into its operating position into the ray path, then the instrument can be used as a full-fledged ophthalmometer. A mating piece which fits into the dovetail receiver of the main objective mount can, however, also be fastened to some other ophthalmological instrument, for instance an endothelium microscope or a Placido light source so that—together with the binocular telescopic magnifier—other ophthalmological examining instruments can be obtained.

In one advantageous embodiment, the mount of the main objective is of rectangular contour, its upper side bearing a two-part protective lid, each part being capable of swinging about a horizontal axis and the front part covering the main objective in a position of rest of the main objective swung out of the optical ray path.

The binocular telescopic magnifier is advisedly fastened to a support which is provided with a hole to receive a correspondingly shaped attachment piece of the downwardly swingable ophthalmological instrument or partial instrument. In this way this instrument is fixed in its position of rest.

Furthermore, it is advantageous to provide tubes in the support to receive current-supply cables. These cables can be connected with the ophthalmometer light and a microswitch for the slit lamp.

The advantages obtained with the invention reside in particular in the fact that the part of the instrument which is swung out of the ray path into its position of rest does not interfere with the ophthalmologist in the space in front of the eye of the patient and that the change from one examination instrument to the other requires practically merely one simple manipulation. One embodiment of the invention is shown in the drawing and will be described in further detail below.

Figure 1:
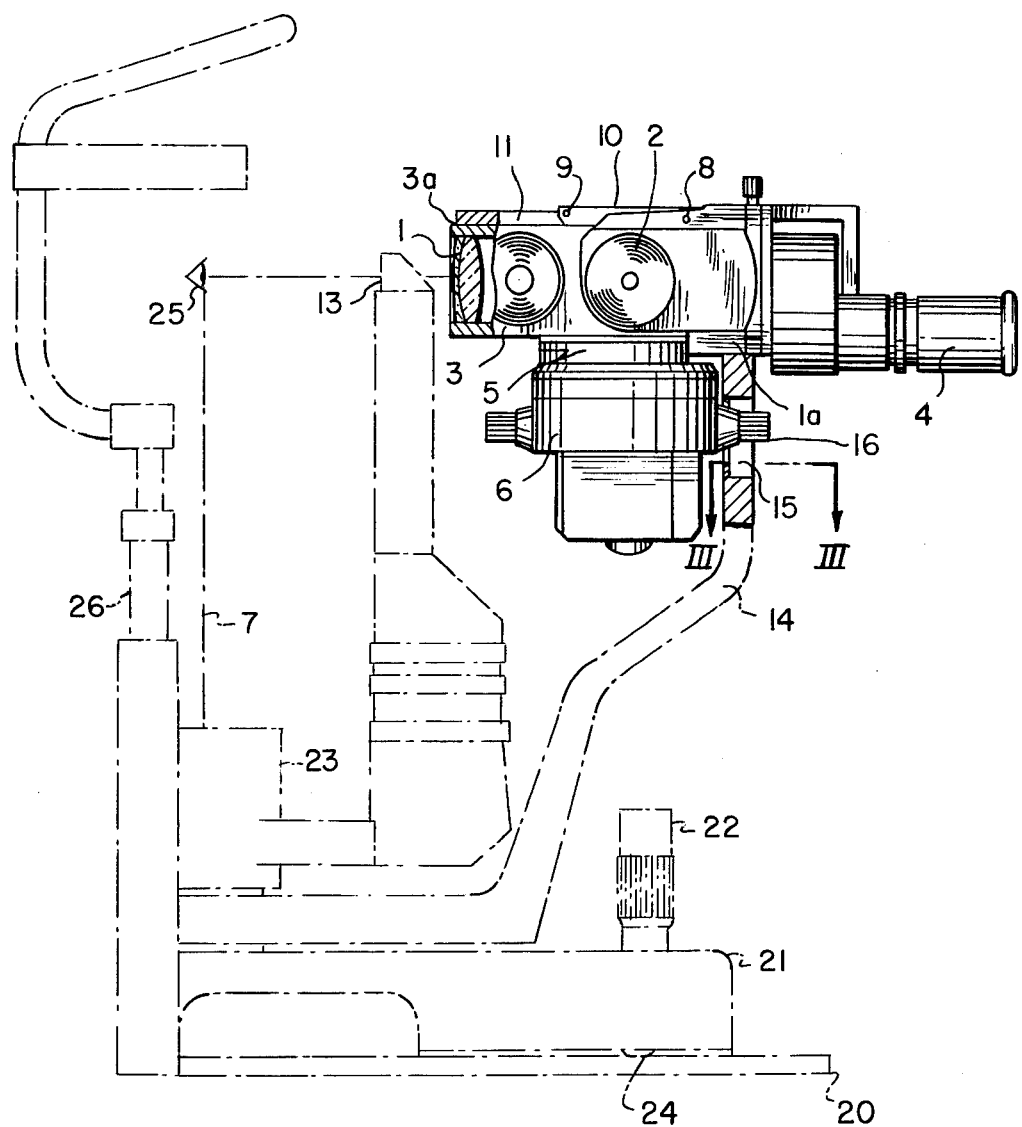
FIG. 1 is a side view of the instrument with main objective of the binocular telescopic magnifier swung into the ray path.
Figure 2:
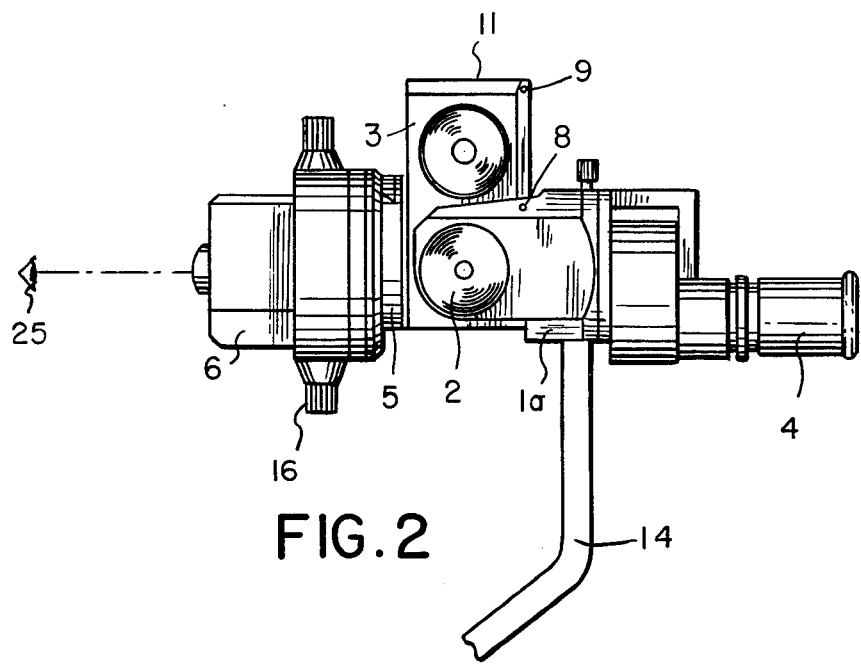
FIG. 2 is a partial view of the side of the instrument with the ophthalmometer attachment swung into the ray path.
Figure 3:
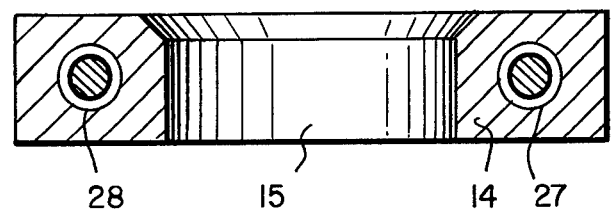
FIG. 3 is a section along the line III—III of FIG. 1, on a larger scale.

In FIG. 1, 20 is the base plate of the instrument. On the base plate there is a slide 21 which upon the swinging of the control lever 22 can be displaced via balls 24 in the horizontal direction. Upon the turning of the control bar 22 the instrument column 23 moves in vertical direction. The support 14 for the binocular telescopic magnifier and the slit lamp 13 which is swingable around a vertical axis 7 are connected with the instrument column. To the left of the slit lamp there is a head rest 26 for fixing the position of the head of the patient and his eye 25. The individual parts of this head rest have not been shown in detail. The eyepiece tubes 4 of the binocular telescopic magnifier are fastened via a fixed part 1a of the objective tube with the support 14 which in its turn is fastened to the column 23. In the slit-lamp combination of the invention shown in FIG. 1, the main objective 1 of the binocular telescopic magnifier is located in the optical ray path (operating position). The main objective 1 is arranged in the mount 3, 3a the outer periphery of which is square. On the top of the objective mount there is a two-part protective lid whose parts 10, 11 are swingable around the horizontal axes 8, 9. The dovetail receiver 5 is fastened to the bottom of the objective mount. In the operating position of the slit lamp of the combination instrument, the ophthalmometer part 6 attached to the dovetail receiver 5 is swung downward into its position of rest and engages by the attachment piece 16 into the hole 15 of the support 14, whereby it is fixed in this position. In FIG. 2 the main objective is shown swung upward in its mount 3, 3a into its position of rest, covered by the protective lid 11. The ophthalmometer part 6 is swung into the optical ray path and is thus in its operating position. Instead of the ophthalmometer part 6 other instrument parts can be inserted in the dovetail receiver 5 and be combined in their use with the slit lamp by swinging into and out of position, for instance an endothelium microscope or a Placido light source. The tubes cast in the support 14 for the passage of current supply cables are designated 27 and 28 in the sectional showing of FIG. 3.

I claim:

1. An improved eye testing apparatus adapted for interchangeable optical functions comprising in combination a binocular telescope magnifier and an ophthalmological examining instrument, wherein the main objective lens of the binocular telescope magnifier is positioned in a mount having a rectangular circumference, said mount being adapted to pivot about a horizontal axis to a first and second predetermined position said horizontal axis being orthogonal to the optical axis, and said first predetermined position being such that the optical axis of said main lens is aligned with the optical ray path, said second predetermined position being such that said main objective lens is displaced rectangularly upward and out of its position of alignment, said mount being provided with a connection means for the detachable connection of the ophthalmological instrument, said ophthalmological instrument being positioned such that in the second predetermined position its optical axis is axially aligned with the optical ray path; said mount being further provided on its upper side with a two-piece protective cover, each piece of said cover being pivotable about a horizontal axis such that the first piece of said two-piece protective cover may be displayed upwardly such that the second piece of said two-piece cover overlies and protects the main objective lens when said mount is in the second predetermined position.

2. An instrument according to claim 1, wherein the binocular telescope magnifier cooperates with a slit lamp when said mount is in the first predetermined position and said slit lamp is rotatable about a vertical axis such that it may be selectively moved from a position of axial alignment to a position of non-alignment with the optical ray path.

3. An instrument according to claim 2, wherein said ophthalmological instrument is selected from the group of an ophthalmometer, an endothelium microscope and a Placido light source.

4. An instrument according to claim 1, wherein said connecting means is a dovetail joint.

* * * * *